United States Patent [19]
Bombardelli et al.

[11] Patent Number: 5,989,557
[45] Date of Patent: Nov. 23, 1999

[54] PROCESS FOR EXTRACTING POLYPHENOL FRACTIONS OF TEA AND COMPOSITIONS PRODUCED THEREWITH

[75] Inventors: Ezio Bombardelli; Paolo Morazzoni; Giuseppe Mustich, all of Milan, Italy

[73] Assignee: Indena S.p.A., Milan, Italy

[21] Appl. No.: 08/930,406

[22] PCT Filed: Mar. 7, 1996

[86] PCT No.: PCT/EP96/00973

§ 371 Date: Sep. 8, 1997

§ 102(e) Date: Sep. 8, 1997

[87] PCT Pub. No.: WO96/28178

PCT Pub. Date: Sep. 19, 1996

[30] Foreign Application Priority Data

Mar. 14, 1995 [IT] Italy .................................. MI95A0493

[51] Int. Cl.$^6$ .............................. A61K 35/78; A23F 3/16; A23F 3/22

[52] U.S. Cl. .................. 424/195.1; 424/456; 424/474; 424/439; 426/431; 426/435; 426/425; 426/427; 426/428; 426/489; 426/492; 426/478; 426/481; 426/541; 426/542

[58] Field of Search .................. 424/439, 195.1, 424/456, 474; 426/431, 435, 425, 427, 428, 489, 492, 478, 481, 541, 542

[56] References Cited

U.S. PATENT DOCUMENTS

| | | | |
|---|---|---|---|
| 4,248,789 | 2/1981 | Okada ................................. | 260/345.2 |
| 4,315,036 | 2/1982 | Husaini et al. ...................... | 426/387 |
| 4,331,694 | 5/1982 | Izod ..................................... | 426/422 |
| 4,411,923 | 10/1983 | Hulbert et al. ...................... | 426/271 |
| 4,521,438 | 6/1985 | Zeller et al. ......................... | 426/271 |
| 4,673,530 | 6/1987 | Hara ..................................... | 252/398 |
| 4,840,966 | 6/1989 | Hara et al. ........................... | 514/456 |
| 5,503,724 | 4/1996 | Crose et al. ......................... | 204/554 |
| 5,527,552 | 6/1996 | Todd, Jr. .............................. | 426/541 |
| 5,674,477 | 10/1997 | Ahluwalia ........................... | 424/70.1 |

FOREIGN PATENT DOCUMENTS

| | | |
|---|---|---|
| 1 097 411 | 1/1995 | China . |
| 167 399 | 1/1986 | European Pat. Off. . |
| 03 027 248 | 2/1991 | Japan . |
| 03 228 664 | 10/1991 | Japan . |
| 07 179 353 | 7/1995 | Japan . |

*Primary Examiner*—Leon B. Lankford, Jr.
*Assistant Examiner*—Christopher R. Tate
*Attorney, Agent, or Firm*—Pennie & Edmonds LLP

[57] ABSTRACT

The present invention relates to the preparation of novel polyphenol fractions of *Camellia sinensis* (tea), the use thereof and formulations containing them. The invention relates specifically to the preparation of extracts deprived of caffeine but containing the polyphenols deriving from epigallocatechin in a natural ratio. The use of these novel extracts, alone or in combination with other active principles, is of interest to the food, pharmaceutical, and cosmetic industry, especially to treat cytotoxic and oxidative conditions.

26 Claims, No Drawings

PROCESS FOR EXTRACTING POLYPHENOL FRACTIONS OF TEA AND COMPOSITIONS PRODUCED THEREWITH

TECHNICAL FIELD

The present invention relates to novel polyphenol fractions of *Camellia sinensis* (tea), the process for the preparation and use thereof, as well as to formulations containing such fractions.

BACKGROUND OF THE INVENTION

More particularly, the invention relates to a process for preparing substantially caffeine-free extracts containing polyphenols derived from epigallocatechin in their natural ratio.

Caffeine is known to have undesirable effects on the cardiovascular system as well as a mutagenic effect, and it is usually removed from such polyphenol fractions by extraction with carbon dioxide under hypercritical condition or with chlorinated solvents. However, the above techniques are not intended to, nor are they capable of, producing extracts with reproducible amounts of the polyphenyl compounds responsible for benificial biological effects.

The polyphenol, characteristic of the tea plant, have recently been the object of a great interest due to their strong antioxidant effect, as described in, for example, Zhao B. et. al., *Cell Biophys.* 14, 175 (1989) and Huang M. T. et al., *Carcinogenesis* 13, 947 (1992). Such an effect is apparently related to some extent to the capability of some of these polyphenols (for example epigallocatechin-3-O-gallate) of inhibiting formation of neoplasias artificially induced in the laboratory animals Conney A. H. et al., *Prev. Med.* 21, 361 (1992) and Mukhtar H. et al., *J. Invest. Dermatol.* 102, 3 (1994).

Moreover, some recent epidemiological studies evidenced how the consumption of large amounts of green tea is associated with a lower incidence of degenerative chronic diseases, for example some forms of cancer and atherosclerosis see, e.g., Kono, S. et al., *Jpn. J. Cancer Res.* 79, 1067 (1988); Oguni I. et al., *Agric. Biol. Chem.* 52, 1879 (1988); Kato I et al., *Jpn. J. Cancer Res.* 81, 1101 (1990) and Kono S. et al., *Prev. Med.* 21, 526 (1992)

At present, the mechanisms of action of the substances contained in green tea derivatives have not yet been completely elucidated, apart from the general antioxidant effect described above. It has however, been determined that the polyphenol component of green tea is capable of exerting a differentiated cytotoxic effect depending on the type of cell which is studied and that such a differentiation is particularly related to the selective targeting which some of these polyphenol molecules have towards sub-cell sites such as mitochondria.

Therefore, there has been a long-felt need, which is now met by the present invention, for a method of extracting *Camellia sinensis* that produces extracts containing a predetermined, i.e., "standardized" amount of polyphenols and wherein the caffeine content of these extracts is minimized, if not eliminated totally.

SUMMARY OF THE INVENTION

The invention therefore is directed, in a first embodiment, to a process for extracting polyphenol fractions from *Camellia sinensis*, which fractions contain no more than about 0.2% by weight of caffeine. The extraction process comprises the steps of: providing a vegetable biomass of *Camellia sinensis* containing a quantity of polyphenols; extracting the vegetable biomass with a hydrated solvent, e.g., a water-alcohol or a water-ketone mixture; at least partially evaporating the solvent to form a residue; adding to the residue thus produced an aqueous mixture of from about 30–60% by volume of methanol to form a suspension of the residue; extracting the hydromethanol suspension with at least one chlorinated solvent, e.g., methylene chloride; filtering and concentrating the hydromethanol phase thus obtained; extracting the concentrated hydromethanol phase with at least one solvent from the group including aliphatic esters, alcohols and ketones, with the proviso that the solvent is substantially immiscible with the hydromethanol phase; concentrating the solvent phase from the immediately preceding extraction step; diluting the concentrated solvent phase with at least one chlorinated solvent; and treating the diluted solvent phase with at least one sulfonic acid resin in an anhydrous medium to remove additional caffeine.

In an alternative embodiment the sulfonic acid resin treatment step may be rendered unnecessary by the interposition of two alternative treatment steps, namely: acidifying the filtered, concentrated hydromethanol phase prior to extraction with the immiscible solvent, i.e., by the addition of at least one organic acid (e.g., a mixture of citric acid and ammonium citrate); and adding an aromatic or aliphatic hydrocarbon, e.g., toluene, in an amount of from about 2 to about 20% by volume to the extracted hydromethanol phase, followed by washing with a dilute, aqueous mineral acid such as sulfuric acid.

Another embodiment concerns a composition comprising polyphenol fractions produced according to any of the methods described above which comprises no more than about 0.2% by weight caffeine. One such preferred composition comprises from about 50 to about 65% epigallocatechin-3-O-gallate, from about 13 to about 20% epicatechin-3-O-gallate, from about 2 to about 4% epicatechin and from about 1.5 to about 3% epigaleocatechin.

A still further embodiment is directed to a method for formulating a composition suitable for pharmaceutical, cosmetic, dietetic or medicament use by a human, which method comprises extracting a quantity of polyphenols sufficient to produce a desired pharmaceutical, cosmetic, dietetic or medicament effect from a vegetable biomass of *Camellia sinensis* by one of the above-described processes; admixing the polyphenol fractions thus obtained with a suitable carrier or excipient; and administering the admixture to a human in an amount sufficient to obtain the described effect. In one embodiment of the invention, the proposed use is as a pharmaceutical and the method further comprises combining the polyphenol fractions with anthracycline, cis-platinum or their derivatives.

DETAILED DESCRIPTION OF THE INVENTION

According to a first embodiment of the process of the invention, the vegetable biomass is extracted with aliphatic alcohols and/or ketones optionally diluted with water. most preferably with aqueous acetone mixtures ranging from 40 to 90% by volume, (particularly with 70% acetone). The resulting extracts may be concentrated to from about 1/5 to about 1/15 of their starting volume. Alternatively, depending upon the solvent used, the solvent may be eliminated entirely.

When the extract is concentrated, the aqueous concentrate is diluted with methanol to 50% (v/v), whereas when the organic solvent is entirely eliminated the residue is suspended in an aqueous methanol mixture ranging from 30 to 60%, preferably 50%. The hydromethanol mixture is counter-extracted with chlorinated solvents, preferably methylene chloride, until elimination of undesired substances such as chlorophyll, terpenes and caffeine not complexed with the oligomeric polyphenols present in the vegetable biomass. The chlorinated organic phases are discarded, whereas the hydromethanol phase is concentrated until methanol is removed, filtering any insolubles comprising tannin complexes with caffeine. The aqueous solution is extracted with immiscible solvents such as aliphatic ketones and alcohols or aliphatic esters. Examples of such solvents comprise methyl ethyl ketone in the presence of salts, such as ammonium chloride or sulfate (which can cleave the complexes with caffeine, due to the acidic and saline nature, thus ensuring that the caffeine remains in the aqueous fraction and at the same time making a selective extraction of the polyphenols possible), butanol in its isomeric forms, ethyl formate or acetate. These solvents, preferably ethyl acetate, allow for a selective recovery of the phenol substances after concentration and dilution with chlorinated solvents, in particular methylene chloride. The resulting extracts still contain an amount greater than 1% of residual caffeine complexed with polyphenols, which can be removed by absorption on sulfonic acid resins in an anhydrous medium, using solvents such as methanol, ethanol or acetone, thereby obtaining an extract containing no more than 0.2% of caffeine.

In a further embodiment, the process of the invention comprises the extraction of the vegetable biomass with 40–50% (v/v) aqueous methanol or acetone, concentrating the eluate until the organic solvent is eliminated, preferably to about the same weight as that of the extracted vegetable material. This concentrate, after filtering off the insolubles, is counter-extracted with chlorinated solvents, preferably methylene chloride, to remove the free caffeine and the terpene-like inert substances. The aqueous solution is acidified with organic acids, preferably citric acid in the presence of ammonium citrate, and counter-extracted with aliphatic esters, preferably ethyl acetate. The organic phase is added with aromatic or aliphatic hydrocarbons in a percentage from 2 to 20% by volume, preferably toluene in a 5% amount by volume based on the total volume of the organic phase, then washed with diluted mineral acids, preferably 1% sulfuric acid, until caffeine is removed.

The organic solution, after washing to neutrality, is concentrated to small volume and poured into a methylene chloride amount sufficient to recover the polyphenols.

The leaves of *Camellia sinensis*, preferably finely ground are used as the vegetable biomass. The extractions are carried out at room temperature (approximately 18–25° C.). The drug/solvent ratio is not critical, but it is generally comprised between 1:1 and 1:5 w/v for each single extraction.

The products obtained according to this process have on the average a content in the most important catechin derivatives of: 50–65% epigallocatechin-3-O-gallate, 13–20% epicatechin-3-O-gallate, 2–4% epicatechin and 1.5–3% epigallocatechin.

The polyphenol fractions obtained according to one of the methods described herein are characterized by an antioxidant power comparable to or higher than that observed for known antioxidants, as is evident from the following Table.

In this "in vitro" test, the anti-lipoperoxidant activity of the products was tested using an experimental model comprising sonication of phosphatidyl choline liposomes in a test tube, and measurement of the products from their oxidative degradation by means of known techniques Maffei-Facino R. et al., *Arzneim.-Forsch./Drug Res.* 44,592 (1994).

The incubation of liposomes in the presence of antioxidants decreases with a dose-related relationship the formation of conjugated dienes, which are a preliminary step of the oxidative degradation of the phospholipids.

TABLE

Antioxidant activity of the polyphenol fraction of green tea on sonicated phosphatidyl choline liposomes (propagation phase). Comparison with epigallocatechin-3-O-gallate, vitamin E and vitamin C

|  | CI50 ($\mu$M) |
| --- | --- |
| Green tea polyphenol fraction* | 0.52 |
| Epigallocatechin-3-O-gallate | 0.50 |
| Vitamin E | 1.25 |
| Vitamin C | inactive |

*assuming as molecular weight that of epigallocatechin-3-O-gallate

Data are expressed as product concentrations ($\mu$M) required to decrease by 50% (CI50) the formation of conjugated dienes following sonication of phosphatidyl choline liposomes.

The antioxidant activity of the polyphenols is believed to be also important as far as the antimutagenic effect is concerned, which has recently been described for some polyphenols such as those extracted from grape-seeds Liviero L. et al., *Fitoterapia LXV,* 203 (1994).

Surprisingly, the polyphenols obtained from green tea (though having a high antioxidant activity), at the same concentrations as those antimutagenic for the products extracted from grape-seeds were antimutagenic, turned out to be devoid of said activity. They are, however characterized by a differential cytotoxicity (higher in cell lines in which a mitochondrial mutation is lethal) which is considered by those working in this field to be of great interest.

Such cytotoxicity is different depending on the cell lines used; in tumoral ovary cells, for example, the product of the present invention exerts a cytotoxic effect at concentrations of about 50 $\mu$M, whereas the effect can be measured at much higher concentrations (1000 $\mu$M) when evaluated on normal ovary cells.

In the present state of the art, different hypothesis have been formulated to elucidate the mechanisms on the basis of the spontaneous mutation. One of the most creditable hypotheses, which has recently gained ground, is that some metabolic products of the cell cycle, particularly free radicals, are responsible for the modulation of mitochondrial heredity through peroxidation of the membrane system on which the mitochondrial DNA replication depends Dujon, B., *Mitochondrial Genetics and Functions,* Stratton J. N. et al. (Eds.), Cold Spring Harbor Laboratory, Cold Spring Harbor, N.Y. (1981); DeFlora S. et al., *Mutation Res.* 214, 153 (1989).

In light of these considerations, two classes of compounds are considered very interesting, which even though they use at least partly analogous basic mechanisms (antioxidant activity at the mitochondrion level), act on two different fronts: the antimutagenic (as in the case of grape-seed derivatives) and the differentiate cytotoxic front (as in the case of the products of the present invention). Both classes of products can therefore be used in the prophylactic treatment of degenerative diseases such as neoplasias, cardiovascular diseases such as atherosclerosis and arthritic and arthrosis forms of various origin.

Moreover, the products of the present invention can be used in therapy, alone or combined with other substances so as to exert a synergistic effect. In oncology, for example, the products can be combined with the usual chemotherapy with the double advantage of both diminishing the oxidative damage which generally is involved in some treatments (for example with some anthracyclines or platinum complexes, such as cis-platinum) and destroying a part of the tumor cells, through a differential cytotoxic mechanism.

In preventing the neoplastic event, the polyphenol fraction taken with the diet is an effective means to destroy mutated cells in the pre-cancer condition. In other conditions, such as atherosclerosis, the products of the invention can advantageously be combined with other antioxidants such as carotenoids, particularly lycopene and zeaxanthin in order to preserve and maintain the integrity of the physiological antioxidant pool.

In articular degenerative conditions, the products of the present invention can be combined with sulfurated amino acids such as methionin, cysteine or proline and hydroxyproline and optionally administered in admixture with glucosamine and jaluronic acid. The role played by the polyphenol fraction in the combination is both antioxidative and antidegenerative on chondroblasts, due to the stimulation of synthesis of collagene and proteoglicans, in the presence of synergizing agents.

The active dosages of these extracts range from 10 to 1000 mg/day, one to four times a day, preferably 50 to 300 mg/day once to twice a day. The oral $DL_{50}$ is above 2000 mg/kg in rats and mice.

The products can be incorporated in the conventional pharmaceutical forms, such as soft- or hard- gelatin capsules, tablets, sachets, syrups, suppositories and vials. In instances where the compositions of the invention are combined with other active ingredients, the compositions of the invention will optionally be suitable for the sequential or separate administration of the single active components.

EXAMPLES

The following examples further illustrate the invention. These examples are provided only for the purpose of illustrating the invention and do not limit the invention in any manner.

Example I
Preparation of Decaffeinated Extracts of Green Tea Containing Standardized Amounts of Polyphenols 1 kg of non-fermented, finely ground leaves of *Camellia sinensis* are extracted 4 times with 3 l each of an acetone/water 7:3 (v/v) mixture. The combined extracts are concentrated to 1 kg under vacuum at a temperature not higher than 45° C. During the concentration, an abundant gummy mass forms, consisting of chlorophyll and other undesired lipohilic substances which contain polyphenols. The concentrate is diluted with 1 l of a methanol/water 1:1 mixture and 0.5 l of methylene chloride. The gummy mass is dissolved in the medium and, after 30 minutes stirring, the phases are separated; the extraction with methylene chloride is repeated 3 more times and then the chloromethylene phase is discarded. The hydromethanol phase is concentrated under vacuum until the methanol is eliminated and the concentrate is extracted 3 times with 0.5 l of ethyl acetate. The aqueous phase is discarded whereas the organic one is dried over $Na_2SO_4$ and concentrated to a small volume (0.22 l). The concentrate is poured into 1.2 l of methylene chloride under strong stirring to obtain an abundant brownish precipitate which, after drying under vacuum, weighs about 0.12 kg.

This residue contains 1.6% of alkaloids and is subjected to a final purification by dissolving it in 1.5 l of methanol, under a nitrogen atmosphere. The methanol solution is treated with 250 ml of the sulfonic acid resin Amberlyst® until the caffeine disappears, which is checked by thin layer chromatography. The methanol solution is concentrated to dryness under vacuum at a temperature not above 50° C. According to this procedure, 0.11 kg of a beige product is obtained, having the following composition:

| | |
|---|---|
| Epigallocatechin-3-O-gallate | 58.0% |
| Epicatechin-3-O-gallate | 16.0% |
| Epicatechin | 3.0% |
| Epigallocatechin | 2.5% |

Example II
Preparation of Decaffeinated Extracts of Green Tea Containing Standardized Amounts of Polyphenols 1 kg of non-fermented, finely ground leaves of *Camellia sinensis* are extracted 4 times with 3 l each of an acetone/water 4:6 mixture. The combined extracts are concentrated to 1 kg under vacuum at a temperature not above 45° C. During the concentration, some precipitate forms which is separated and discarded. The concentrate is extracted three times with 0.5 l of methylene chloride and the chloromethylene phase is then discarded. The aqueous phase is acidified to pH 1.5 with citric acid in the presence of ammonium citrate and extracted 3 times with 0.5 ml of ethyl acetate. The aqueous phase is then discarded whereas the organic phase is diluted with 75 ml of toluene and counter-extracted 3 times with 150 ml each of 1% $H_2SO_4$. After washing with water to neutrality and drying over $Na_2SO_4$, the organic phase is concentrated to 300 ml and the concentrate is then poured into 1.5 ml of methylene chloride. After drying under vacuum overnight, 0.1 kg of a beige powder is obtained, having the characteristics of the product of example I.

Example III
Preparation of Decaffeinated Extracts of Green Tea Containing Standardized Amounts of Polyphenols 1 kg of non-fermented, finely ground leaves of *Camellia sinensis* are extracted 4 times with 3 l each of a methanol/water 1:1 mixture. The combined extracts are concentrated to 1 kg under vacuum at a temperature not above 45° C. During the concentration, some precipitate forms which is separated and discarded. The concentrate is extracted three times with 0.5 l of methylene chloride and the chloromethylene phase is then discarded. The aqueous phase is acidified to pH 1.5 with citric acid In the presence of ammonium citrate and extracted 3 times with 0.5 l of ethyl acetate. The aqueous phase is then discarded whereas the organic phase is diluted with 75 ml of toluene and counter-extracted 3 times with 150 ml each of 1% $H_2SO_4$. After washing with water to neutrality and drying over $Na_2SO_4$, the organic phase is concentrated to 300 ml and the concentrate is then poured into 1.5 ml of methylene chloride. After drying under vacuum at 50° C. overnight, 0.1 kg of a beige powder is obtained, having the characteristics of the product of example I.

Example IV
Gelatin Capsules Containing the Polyphenol Fraction of Green Tea 50 mg of polyphenol fraction of green tea are mixed with 88 mg of microcrystalline cellulose (Avicel PH 102), 3 mg of colloidal silica (Aerosil 200), 8 mg of cross-linked sodium carboxymethyl cellulose (Ac-Di-Sol) and 1 mg of magnesium stearate. The resulting mixture is encapsulated in hard-gelatin capsules (Size 3).

Example V

Gelatin Capsules Containing the Polyphenol Fraction of Green Tea 150 mg of polyphenol fraction of green tea are mixed with 264 mg of microcrystalline cellulose (Avicel PH 102), 9 mg of colloidal silica (Aerosil 200), 24 mg of cross-linked sodium carboxymethyl cellulose and 3 mg of magnesium stearate. The resulting mixture is encapsulated in hard-gelatin capsules (Size 0).

Example VI

Coated Tablets Containing the Polyphenol Fraction of Green Tea 50 mg of polyphenol fraction of green tea are mixed with 50 mg of microcrystalline cellulose (Avicel PH 101), 33 mg of dibasic calcium phosphate (Emcompress A), 3 mg of colloidal silica (Aerosil 200), 12 mg of cross-linked sodium carboxymethyl cellulose (Ac-Di-Sol) and 2 mg of magnesium stearate. The powders are mixed for 10 minutes, then tabletted dosing at 150 mg/tablet. The resulting tablets (diameter: 7 mm) are coated with a film layer containing 4.5 mg of hydroxypropylmethyl cellulose (Methocel E5), 0.9 mg of Polyethylene glycol 6000 (Carbowax 6000), 1.2 mg of titanium dioxide and 0.9 mg of talc.

Example VII

Coated Tablets Containing the Polyphenol Fraction of Green Tea 150 mg of polyphenol fraction of green tea are mixed with 150 mg of microcrystalline cellulose (Avicel PH 101), 99 mg of dibasic calcium phosphate (Emcompress A), 9 mg of colloidal silica (Aerosil 200), 36 mg of cross-linked sodium carboxymethyl cellulose (Ac-Di-Sol) and 6 mg of magnesium stearate. The powders are mixed for 10 minutes, then tabletted dosing at 450 mg/tablet. The resulting tablets (diameter: 11 mm) are coated with a film layer containing 13.5 mg of hydroxypropylmethyl cellulose (Methocel E5), 2.7 mg of Polyethylene glycol 6000 (Carbowax 6000), 3.6 mg of titanium dioxide and 2.7 mg of talc.

Example VIII

Vials Containing the Polyphenol Fraction of Green Tea.

10 mg of polyphenol fraction of green tea are mixed with 200 mg of glucose and dissolved in water for injectable preparations q.s. to 5 ml. This solution (pH 4.5) can then be used for the preparation of injectable vials to be prepared with conventional techniques.

We claim:

1. A process for extracting polyphenol fractions from *Camellia sinensis*, which fractions cumulatively contain no more than about 0.2% by weight of caffeine, said process comprising:
   (a) providing a vegetable biomass of *Camellia sinensis* containing a quantity of polyphenols;
   (b) extracting the vegetable biomass with a hydrated organic solvent;
   (c) at least partially evaporating the solvent;
   (d) adding to a residue produced upon said at least partial evaporation an aqueous mixture of from about 30–60% by volume of methanol to form a hydromethanol suspension of said residue;
   (e) extracting the hydromethanol suspension with at least one chlorinated solvent;
   (f) filtering and then concentrating the hydromethanol phase obtained upon extraction with said at least one chlorinated solvent;
   (g) extracting the concentrated hydromethanol phase with at least one solvent selected from the group consisting of aliphatic esters, alcohols and ketones wherein said at least one solvent is substantially immiscible with the hydromethanol phase;
   (h) concentrating the solvent phase from the immediately preceding extraction step;
   (i) diluting said concentrated solvent phase with at least one chlorinated solvent;
   (j) treating said diluted solvent phase with at least one sulfonic acid resin in an anhydrous medium to remove additional caffeine; and
   (k) isolating said polyphenol fractions from said diluted solvent phase to permit recovery of said fractions substantially free of said solvent, wherein each said extraction step is carried out at substantially ambient temperature.

2. The process of claim 1 which further comprises acidifying the filtered, concentrated hydromethanol phase before extracting with said immiscible solvent.

3. The process of claim 2 wherein the hydromethanol phase is acidified by adding at least one organic acid.

4. The process of claim 3 wherein said organic acid comprises a mixture of citric acid and ammonium citrate.

5. The process of claim 1, which further comprises adding an aromatic or aliphatic hydrocarbon to the extracted hydromethanol phase of step (g), followed by washing with a dilute, aqueous mineral acid.

6. The process of claim 5, wherein the hydrocarbon is added in an amount of from about 2 to about 20% by volume.

7. The process of claim 6 wherein said hydrocarbon is toluene and wherein the toluene is added in an amount of about 5% by volume, based upon the total volume of the organic phase.

8. The process of claim 5 wherein said washing step is carried out with a solution of about 1% sulfuric acid.

9. The process of claim 1 wherein the solvent of step (b) is selected from the group consisting of water-alcohol and water-ketone mixtures.

10. The process of claim 9 wherein the vegetable biomass is extracted with from about 40 to about 90% by volume of aqueous acetone.

11. The process of claim 10 wherein the vegetable biomass is extracted with about 70% by volume of aqueous acetone.

12. The process of claim 1 wherein the suspension is formed with the addition of about 50% by volume of aqueous methanol.

13. The process of claim 1 wherein methylene chloride is selected as the chlorinated solvent.

14. The process of claim 1 wherein said at least one solvent of step (g) is selected from the group consisting of ethyl acetate, ethyl formate, methyl ethyl ketone, 1-butanol, tert-butanol and 2-butanol.

15. The process of claim 14 wherein said at least one solvent of step (g) is ethyl acetate.

16. A process for extracting polyphenol fractions from *Camellia sinensis* which fractions cumulatively contain no more than about 0.2% by weight of caffeine, said process comprising:
   (a) providing a vegetable biomass of *Camellia sinensis* containing a quantity of polyphenols;

(b) extracting the vegetable biomass with a hydrated organic solvent;
(c) at least partially evaporating the solvent;
(d) adding to a residue produced upon said at least partial evaporation an aqueous mixture of from about 30–60% by volume of methanol to form a hydromethanol suspension of said residue;
(e) extracting the hydromethanol suspension with at least one chlorinated solvent;
(f) filtering and then concentrating the hydromethanol phase obtained upon extraction with said at least one chlorinated solvent;
(g) acidifying the filtered, concentrated hydromethanol phase by the addition thereto of at least organic acid;
(h) extracting the acidified hydromethanol phase with at least one solvent selected from the group consisting of aliphatic esters, alcohols and ketones, wherein said at least one solvent is substantially immiscible with the hydromethanol phase;
(i) adding to said extracted hydromethanol phase an aromatic or aliphatic hydrocarbon, followed by washing with a dilute, aqueous mineral acid;
(j) concentrating the solvent phase from the immediately preceding extraction step;
(k) diluting said concentrated solvent phase with at least one chlorinated solvent; and
(l) isolating said polyphenol fractions from said diluted solvent phase to permit recovery of said fractions substantially free of said solvent, wherein each said extraction step is carried out at substantially ambient temperature.

17. A method for formulating a composition suitable for use as a pharmaceutical, cosmetic dietetic or medicament by a human, which method comprises:
    extracting a quantity of polyphenols from a vegetable biomass of *Camellia sinensis* sufficient to produce a desired pharmaceutical, cosmetic, dietetic or medicament effect in said human; and
    admixing said polyphenols with a suitable carrier or excipient,
    wherein said polyphenols are extracted by
        (a) providing a vegetable biomass of *Camellia sinensis* containing a quantity of polyphenols;
        (b) extracting the biomass with a hydrated organic solvent;
        (c) at least partially evaporating the solvent;
        (d) adding to a residue produced upon said at least partial evaporation an aqueous mixture of from about 30–60% by volume of methanol to form a hydromethanol suspension of said residue;
        (e) extracting the hydromethanol suspension with at least one chlorinated solvent;
        (f) filtering and then concentrating the hydromethanol phase obtained upon extraction with said at least one chlorinated solvent;
        (g) extracting the concentrated hydromethanol phase with at least one solvent selected from the group consisting of aliphatic esters, alcohols and ketones, wherein said at least one solvent is substantially immiscible with the hydromethanol phase;
        (h) concentrating the solvent phase from the immediately preceding extraction step;
        (i) diluting said concentrating solvent phase with at least one chlorinated solvent;
        (j) treating said diluted solvent phase with at least one sulfonic acid resin in an anhydrous medium to remove additional caffeine and form a composition that cumulatively contains no more than about 0.2% by weight of caffeine; and
        (k) isolating said polyphenol fractions from said diluted solvent phase to permit recovery of said fractions substantially free of said solvent wherein each said extraction step is carried out at substantially ambient temperature.

18. The method of claim 17 wherein the composition is a pharmaceutical and which further comprises combining said polyphenols with anthracycline or cis-platinum prior to use of the composition as said pharmaceutical.

19. The method of claim 17 wherein said quantity of polyphenols comprises:
    from about 50 to about 65% by weight of epigallocatechin-3-O-gallate;
    from 13 to about 20% by weight of epicatechin-3-O-gallate;
    from about 2 to about 4% by weight epicatechin; and
    from about 1.5 to abut 3% by weight of epigallocatechin.

20. A method of treating a cytotoxic condition in humans, which method comprises administering the admixture of polyphenols recited in claim 19 to a human patient with said condition in an amount sufficient to treat said condition.

21. A method for formulating a composition suitable for use as a pharmaceutical, cosmetic, dietetic or medicament by a human, which method comprises
    extracting a quantity of polyphenols from a vegetable biomass of *Camellia sinensis* sufficient to produce a desired pharmaceutical, cosmetic, dietetic or medicament effect in said human; and
    admixing said polyphenols with a suitable carrier or excipient,
    wherein said polyphenols are extracted by
        (a) providing a vegetable biomass of *Camellia sinensis* containing a quantity of polyphenols;
        (b) extracting the vegetable biomass with a hydrated organic solvent;
        (c) at least partially evaporating the solvent;
        (d) adding to a residue produced upon said at least partial evaporation an aqueous mixture of from about 30–60% by volume of methanol to form a hydromethanol suspension of said residue;
        (e) extracting the hydromethanol suspension with at least one chlorinated solvent;
        (f) filtrating and then concentrating the hydromethanol phase obtained upon extraction with said at least one chlorinated solvent;
        (g) acidifying the filtered, concentrated hydromethanol phase by the addition thereto of at least one organic acid;
        (h) extracting the acidified hydromethanol phase with at least one solvent selected from the group consisting of aliphatic esters, alcohols and ketones, wherein said at least one solvent is substantially immiscible with the hydromethanol phase;
        (i) adding to said extracted hydromethanol phase an aromatic or aliphatic hydrocarbon, followed by washing with a dilute, aqueous mineral acid;
        (j) concentrated the solvent phase from the immediately preceding extraction step;
        (k) diluting said concentrated phase with at least one chlorinated solvent to form a composition that cumulatively contains no more than about 0.2% by weight of caffeine; and
        (l) isolating said polyphenol fractions from said diluted solvent phase to permit recovery of said fractions substantially free of said solvent wherein each said extraction step is carried out at substantially ambient temperature.

22. The method of claim 21 wherein the composition is a pharmaceutical and which further comprises combining said polyphenols with anthracycline or cis-platinum prior to use of the composition as said pharmaceutical.

23. The method of claim 21 wherein said quantity of polyphenols comprises:
   from about 50 to about 65% by weight of epigallocatechin-3-O-gallate;
   from about 13 to about 20% by weight of epicatechin-3-O-gallate;
   from about 2 to about 4% by weight epicatechin; and
   from about 1.5 to about 3% by weight of epigallocatechin.

24. A method of treating a cytotoxic condition in humans, which method comprises administering the admixture of polyphenols recited in claim 23 to a human patient with said condition in an amount sufficient to treat said condition.

25. A method of treating a cytotoxic condition in humans, which method comprises:
   extracting a quantity of polyphenols from a vegetable biomass of *Camellia sinensis* sufficient to treat said condition, said quantity of polyphenols comprising
      from about 50 to about 65% by weight of epigallocatechin-3-O-gallate;
      from about 13 to about 20% by weight of epicatechin-3-O-gallate;
      from about 2 to about 4% by weight of epicatechin; and
      from about 1.5 to about 3% by weight of epigallocatechin;
   admixing said polyphenols with a suitable carrier or excipient; and
   administering said admixture to said human in an amount sufficient to treat said condition,
   wherein said polyphenols are extracted by
      (a) providing a vegetable biomass of *Camellia sinensis* containing a quantity of polyphenols;
      (b) extracting the biomass with a hydrated organic solvent;
      (c) at least partially evaporating the solvent;
      (d) adding to a residue produced upon said at least partial evaporation an aqueous mixture of from about 30–60% by volume of methanol to form a hydromethanol suspension of said residue;
      (e) extracting the hydromethanol suspension with at least one chlorinated solvent;
      (f) filtering and then concentrating the hydromethanol phase obtained upon extraction with said at least one chlorinated solvent;
      (g) extracting the concentrated hydromethanol phase with at least one solvent selected from the group consisting of aliphatic esters, alcohols and ketones, wherein said at least one solvent is substantially immiscible with the hydromethanol phase;
      (h) concentrating the solvent phase from the immediately preceding extraction step;
      (i) diluting said concentrating solvent phase with at least one chlorinated solvent;
      (j) treating said diluted solvent phase with at least one sulfonic acid resin in an anhydrous medium to remove additional caffeine and form a composition that cumulatively contains no more than about 0.2% by weight of caffeine; and
      (k) isolating said polyphenol fractions from said diluted solvent phase to permit recovery of said fractions substantially free of said solvent, wherein each said extraction step is carried out at substantially ambient temperature.

26. A method of treating a cytotoxic condition in humans, which method comprises:
   extracting a quantity of polyphenols from a vegetable biomass of *Camellia sinensis* sufficient to treat said condition, said quantity of polyphenols comprising
      from about 50 to about 65% by weight of epigallocatechin-3-O-gallate;
      from about 13 to about 20% by weight of epicatechin-3-O-gallate;
      from about 2 to about 4% by weight of epicatechin; and
      from about 1.5 to about 3% by weight of epigallocatechin,
   admixing said polyphenols with a suitable carrier or excipient; and
   administering said admixture to said human in an amount sufficient to treat said condition,
   wherein said polyphenols are extracted by
      (a) providing a vegetable biomass of *Camellia sinensis* containing a quantity of polyphenols;
      (b) extracting the vegetable biomass with a hydrated organic solvent;
      (c) at least partially evaporating the solvent;
      (d) adding to a residue produced upon said at least partial evaporation an aqueous mixture of from about 30–60% by volume of methanol to form a hydromethanol suspension of said residue;
      (e) extracting the hydromethanol suspension with at least one chlorinated solvent;
      (f) filtrating and then concentrating the hydromethanol phase obtained upon extraction with said at least one chlorinated solvent;
      (g) acidifying the filtered, concentrated hydromethanol phase by the addition thereto of at least one organic acid;
      (h) extracting the acidified hydromethanol phase with at least one solvent selected from the group consisting of aliphatic esters, alcohols and ketones, wherein said at least one solvent is substantially immiscible with the hydromethanol phase;
      (i) adding to said extracted hydromethanol phase an aromatic or aliphatic hydrocarbon, followed by washing with a dilute, aqueous mineral acid;
      (j) concentrated the solvent phase from the immediately preceding extraction step;
      (k) diluting said concentrated phase with at least one chlorinated solvent to form a composition that cumulatively contains no more than about 0.2% by weight of caffeine; and
      (l) isolating said polyphenol fractions from said diluted solvent phase to permit recovery of said fractions substantially free of said solvent, wherein each said extraction step is carried out at substantially ambient temperature.

* * * * *